United States Patent [19]

Steffen

[11] Patent Number: 5,869,737
[45] Date of Patent: Feb. 9, 1999

[54] PROCESS FOR THE PREPARATION OF CYCLOPROPANE-1, 1-DICARBOXYLIC ACID DERIVATIVES

[75] Inventor: Klaus-Dieter Steffen, Hennef, Germany

[73] Assignee: Huels Aktiengesellschaft, Marl, Germany

[21] Appl. No.: 910,895

[22] Filed: Aug. 13, 1997

[30] Foreign Application Priority Data

Aug. 17, 1996 [DE] Germany .................. 196 33 168.4

[51] Int. Cl.$^6$ ................................... C07C 69/74
[52] U.S. Cl. .................. 560/124; 558/357; 562/506; 564/152
[58] Field of Search .................. 560/124; 562/506; 558/357; 564/152

[56] References Cited

U.S. PATENT DOCUMENTS 5,510,509  4/1996  Steffen ............................. 560/124

OTHER PUBLICATIONS

Dox, J. Am. Chem. Soc., vol. 43, pp. 2097–2101, 1921.
Perkin, J. Chem. Soc., vol. 65, pp. 572–591, 1894.

*Primary Examiner*—Michael L. Shippen
*Attorney, Agent, or Firm*—Oblon, Spivak, McClelland, Maier & Neustadt, P.C.

[57] ABSTRACT

A cyclopropane-1,1-dicarboxylic acid compound is prepared by reacting a malonic acid compound and a 1,2-dihalogeno compound with an alcoholate as a condensation agent which is gradually added to a mixture of said malonic acid compound and said 1,2-chloro compound as a solution or suspension is an alcohol.

14 Claims, No Drawings

PROCESS FOR THE PREPARATION OF CYCLOPROPANE-1, 1-DICARBOXYLIC ACID DERIVATIVES

BACKGROUND OF THE INVENTION

1. Field of the Invention

The present invention relates to a process for the preparation of cyclopropane-1,1-dicarboxylic acid derivatives from malonic acid derivatives and 1,2-dichloro compounds.

2. Description of the Background

Cyclopropane-1,1-dicarboxylic acid derivatives are valuable starting materials for the manufacture of drugs and plant protection agents (see e.g. EP 0 512 211, DE 41 14 733, U.S. Pat. No. 5,334,747).

Diethyl cyclopropane-1,1-dicarboxylate was first prepared by W. H. Perkin (Ber. d. Dt. Chem. Ges., 17 (1884), 54) by means of an intramolecular condensation reaction between diethyl malonate and 1,2-dibromoethane with sodium ethylate as the condensation agent. The yield was 27 to 29% of theory. A. W. Dox and L. Yoder (J.A.C.S., 1921, 2097) were able to increase the yield to 40% of theory, as confirmed by J. M. Stewart and H. H. Westberg (J. Org. Chem., 30 (1965), 1951). One disadvantage of this process is its low yield. The main by-product identified by W. A. Bone and W. H. Perkin (J. Chem. Soc., 67 (1895), 108) is tetraethyl butane-1,1,4,4-tetracarboxylate, which is formed in a competing intermolecular reaction. When using 1,2-dichloroethane, as an alternative to 1,2-dibromoethane, which is a desirable alternative to the 1,2-dibromo compound because it is a cheaper starting material available in industrial quantities, the yield of this by-product can increase to as much as 50% of theory.

Another disadvantage of the process, according to J. M. Stewart and W. H. Westberg, loc. cit., is the difficulty of separating unreacted malonic acid ester by distillation. The authors solved this problem by reacting the malonic acid ester with n-butylamine to give the corresponding n-butyldiamide.

The disadvantages mentioned are considerably alleviated by using potassium carbonate in place of a sodium alcoholate as the condensation agent (D. A. White, Synth. Comm., 7/8 (1977), 559). Yields of dimethyl cyclopropane-1,1-dicarboxylate of 73% of theory are indicated when 1,2-dibromoethane is used. An improved process employs potassium carbonate as the base, with 1,2-dichloroethane as the starting material, and is described in DE 43 26 917. Although the yield ranges up to 85% of theory in this process, carbon dioxide is produced in appreciable amounts, as with all processes using potassium carbonate as condensation agent. This waste gas entrains 1,2-dichloroethane, which is of environmental concern and has to be removed in a special purification step. A need therefore continues to exist for a process for the preparation of cyclopropane-1,1-dicarboxylic acid derivatives from malonic acid derivatives and inexpensive 1,2-dichloro compounds, but produces no waste gas, and which also gives even better yields than the process of DE 43 26 917.

SUMMARY OF THE INVENTION

Accordingly, one object of the present invention is to provide a process of synthesizing cyclopropane-1,1-dicarboxylic acid derivatives, using 1,2-dichloroethane compounds as a starting material, in markedly improved yields with no by-product production.

Briefly, this object and other objects of the invention as hereinafter will become more readily apparent can be attained by a process of preparing cyclopropane-1,1-dicarboxylic acid derivatives from malonic acid derivatives and 1,2-dichloro compounds, with alcoholates as the condensation agents, by gradually adding a solution or suspension of an alcoholate in an alcohol to a mixture of a malonic acid derivative, a 1,2-dichloro compound and, if appropriate, a solvent.

DETAILED DESCRIPTION OF THE PREFERRED EMBODIMENTS

The process of the invention achieve yields of cyclopropane-1,1-dicarboxylic acid derivatives of almost 90% of theory. No waste gases are produced, in particular no waste gases which must not be discharged into the environment without treatment. Despite the gradual addition of the alcoholate, space-time yields of cyclopropane-1,1-dicarboxylic acid derivatives of up to 10 kg per $m^3$ per hour are achieved. The intramolecular elimination of hydrogen chloride, which is an undesired competing reaction, is extensively suppressed. The products can easily be prepared in high purity suitable for use as precursors for drugs and plant protection agents. Even the salts, which are produced in stoichiometric amounts, are obtained in a re-usable form and do not have to be discarded.

The cyclopropane-1,1-dicarboxylic acid derivatives have the formula

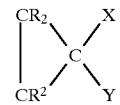

I in which the radicals R can be identical or different and are in each case hydrogen or an organic radical, especially an alkyl radical having 1 to 8 carbon atoms, or two of them together can form an alkylene radical having 5 to 12 carbon atoms, and X and Y can again be identical or different and are a carboxylic acid ester group, especially a carbalkoxy group having 2 to 5 carbon atoms, a nitrile group or an optionally N-substituted carboxamide group. The preferred N-substituted carboxamide groups are N,N-dialkyl-substituted carboxamide groups in which the alkyl radicals have 1 to 4 carbon atoms.

The malonic acid derivatives have the formula:
in which X and Y are defined as indicated. Examples of

II suitable malonic acid derivatives II include dimethyl malonate, diethyl malonate, diisobutyl malonate, di-2-ethylhexyl malonate, malononitrile, methyl cyanoacetate, ethyl cyanoacetate, ethyl carboxamidoacetate, methyl N,N-diethylcarboxamidoacetate and N,N,N',N'-tetramethylmalonic acid diamide. Preferred malonic acid derivatives are the diesters with alkanols having 1 to 4 carbon atoms.

Suitable 1,2-dichloro compounds have the formula:

III in which R is defined as indicated. Suitable examples of 1,2-dichloro compounds III include 1,2-dichloroethane, 1,2-dichloropropane, 1,2-dichlorobutane, 2,3-dichlorobutane, 2,3-dichloropentane, 2-methyl-1,2-dichlorobutane, 1,2- dichlorooctane, 1,2-dichlorocyclopentane, 1,2-dichlorocyclohexane, 1,2-dichlorocyclododecane, 1,2-dichloroethylbenzene and 1,2-dichloroisopropylbenzene.

The reaction is advantageously carried out in the presence of an inert solvent, with preferred inert solvents being N,N-disubstituted carboxamides such as N,N-dimethylformamide and N,N-dimethylacetamide, and N-methylpyrrolidone.

Particularly suitable alcoholate bases include the alkali metal alcoholates, especially sodium alcoholates. The preferred alkali metal alcoholates are derived from alkanols having 1 to 4 carbon atoms. Sodium methylate and sodium ethylate are particularly preferred. The alcoholates are used as a solution or suspension in an alcohol, advantageously in a concentrated form with an alcoholate content of 20 to 40 percent by weight, for example as a 30 percent by weight solution of sodium methylate in methanol. The solvent or suspending agent used for the alcoholate is advantageously the alcohol from which the alcoholate is derived. Accordingly, alkanols having 1 to 4 carbon atoms are preferred. If the starting material II is a malonic acid ester, the alcoholate and alcohol used are advantageously those which correspond to the alcohol of the ester, in order to avoid transesterification.

The starting materials II and III and the alcoholate are advantageously used in molar proportions of 1: (2.0–6.0): (1.6–2.0). Excess alcoholate should be avoided in order to suppress the intramolecular elimination of hydrogen chloride to give e.g. vinyl chloride or allyl chloride. If the reaction is carried out with a solvent, it is advantageously used in an amount ranging from 1 to 3 times the amount by weight of malonic acid ester.

The process is generally carried out at temperatures of 80° to 140° C., especially of 95° to 120° C. The optimum temperature depends on the starting materials II and III used and also on their proportions and can easily be determined in a given case by means of preliminary experiments. To remove the alcohol, the reaction should be carried out at the boiling point of the reaction mixture. The optimum reaction temperature is the determining parameter here. The pressure is therefore adjusted so that the reaction mixture boils at the optimum reaction temperature.

The process of the invention is carried out e.g. by placing the starting materials II and III, and advantageously an inert solvent, in a reactor and heating the mixture to the reaction temperature. The solution or suspension of the alcoholate is then added gradually. The alcohol from the solution or suspension, together with the alcohol released from the alcoholate, distill through a column with the 1,2-dichloro compound, either in proportion to the vapor pressures or as an azeotrope, depending on the alcohol and 1,2-dichloro compound used. The vapors are condensed and the condensate is separated into alcohol and 1,2-dichloro compound by fractional distillation if these substances do not form an azeotrope. If they do form an azeotrope, the condensate is transferred to a phase separation vessel which already contains water for extracting the alcohol. It is possible to continuously pass water into the phase separation vessel and for aqueous alcohol to be drawn off in the corresponding amount. Alternatively, a batch procedure can be employed in which the amount of water sufficient to extract all the alcohol is introduced into the phase separation vessel. If 1,2-dichloroethane is used as the starting material III and sodium methylate in methanol is used as the alcoholate, 40 to 70 parts by weight of water should be present in order to take up about 35 parts by weight of methanol. This amount of methanol corresponds to 100 parts by weight of azeotrope, which consists of 35 parts by weight of methanol and 65 parts by weight of 1,2-dichloroethane.

In order to estimate the optimum amount of water for the extraction process the Table, infra, shows by way of example the compositions of the aqueous (upper) phase and the organic (lower) phase after the uptake of 35 parts by weight of methanol (from 100 parts by weight of azeotrope with 1,2-dichloroethane) as a function of the amount of the amount of water used for extraction:

| Water for extraction [g] | Phase | composition of the phase [% by weight] | | |
| --- | --- | --- | --- | --- |
| | | 1,2-dichloroethane | Methanol | Water |
| 15 | lower phase | 92 | 7 | 1 |
| | upper phase | 22 | 53 | 25 |
| 30 | lower phase | 96.7 | 3 | 0.3 |
| | upper phase | 7 | 48 | 45 |
| 45 | lower phase | 97.8 | 2 | 0.2 |
| | upper phase | 3 | 41 | 56 |
| 60 | lower phase | 98.3 | 1.5 | 0.2 |
| | upper phase | 2 | 35 | 63 |

If the 1,2-dichloro compound and the alcohol do not form an azeotrope, they can be re-used as such after separation by fractional distillation. If they do form an azeotrope, the lower phase obtained on extraction with water, which contains the 1,2-dichloro compound, can be transferred to the top of the column and thereby recycled into the reaction vessel. However, care must be taken here to ensure that the small amount of water present (see above Table) does not reach the reactor and inactivate alcoholate by hydrolysis. The alcohol can be obtained in a re-usable form from the upper, aqueous phase by distillation. The water requires treatment but can be disposed of in a normal biological sewage treatment plant.

The addition of the alcoholate generally takes 5 to 10 hours, depending on the malonic acid derivative II and 1,2-dichloro compound III. It is advantageous to allow the reaction to continue for some time, e.g. about one hour, and then to allow the reaction mixture to cool. The salt which has precipitated out is separated in a conventional manner, e.g. by filtration, with or without pressure, or by centrifugation, and advantageously washed with a solvent and/or with the particular 1,2-dichloro compound used. If a solvent such as dimethylformamide has been used in the reaction, it is of course best to wash the salt with this solvent.

The reaction mixture, from which the salt has been removed, and the wash liquor are advantageously worked up by distillation. Excess 1,2-dichloro compound III and, if appropriate, solvent are the first to be removed by distillation. They can be used in another reaction. Unreacted malonic acid derivative II is removed under reduced pressure via an efficient column. The desired cyclopropane-1,1-dicarboxylic acid derivative I is the last material to distill.

Having generally described this invention, a further understanding can be obtained by reference to certain specific examples which are provided herein for purposes of illustration only and are not intended to be limiting unless otherwise specified.

EXAMPLE 1

Preparation of Methyl Cyclopropane-1,1-dicarboxylate (MCD)

The apparatus consists of a 4 l multinecked flask as reactor, which is fitted with a stirrer, a thermometer, a dropping funnel and a distillation attachment with column. The receiver for the top distillate is in the form of a phase separation vessel from which the lower phase, consisting essentially of 1,2-dichloroethane, is returned to the column. Aqueous alcohol is drawn off continuously from the upper phase and water is introduced in order to maintain a specific level in the vessel.

A 330 g (2.5 mol) amount of dimethyl malonate (DMM), 590 g of dimethylformamide (DMF) and 742 g (7.5 mol) of 1,2-dichloroethane (DCE) are placed in the reactor and heated to 110° C. A 900 g (7.5 mol) amount of a 30 percent by weight solution of sodium methylate in methanol is metered into the stirred mixture over 8 hours. An azeotrope boiling at 70° C. and containing 68 percent by weight of DCE and 32 percent by weight of methanol is removed by distillation under normal pressure. The condensate is passed through an aqueous phase in the phase separation vessel so that the methanol is extracted. Part of the aqueous phase is continuously drawn off and the removed amount is replaced by the introduction of a corresponding amount of water. The lower phase, consisting essentially of DCE, returns back to the top of the column.

When all the sodium methylate has been added, the reaction mixture is allowed to react for a further 30 minutes at 110° C. and cooled to room temperature. The sodium chloride which has precipitated is filtered, washed with dimethylformamide and 1,2-dichloroethane and dried. The sodium chloride is suitable for chloro-alkali electrolysis.

The filtrate and wash liquors are distilled via an efficient column. DCE distills first at normal pressure. DMF and unreacted DMM are then removed by distillation under vacuum and 313.4 g of MCD distill over last at 82° C./16 mbar. Its purity is 99.5% according to GC analysis. The yield is 78% of theory, based on the DMM used. The intermediate fraction contains 30.7 g of unreacted DMM, which can be re-used in a new reaction. The yield is 87% of theory, based on the DMM converted.

EXAMPLES 2 AND 3

Preparation of Methyl Cyclopropane-1,1-dicarboxylate (MCD)

The procedure described in Example 1 is employed except that the amounts of DCE are increased or reduced. As the reaction is carried out in both cases under normal pressure, the reaction temperatures also change. The results are shown in the following Table:

| Example | Molar ratio DMM:DCE | Reaction temperature [°C.] | Yield of MCD [% of theory] based on DMM used | DMM converted |
|---|---|---|---|---|
| 2 | 1:6 | 99–103 | 73.7 | 82.4 |
| 2 | 1:2 | 125–132 | 62.0 | 70.7 |

EXAMPLE 4

Preparation of Ethyl Cyclopropane-1,1-dicarboxylate (ECD)

The apparatus described in Example 1 is used. A mixture of 400.5 g (2.5 mol) of diethyl malonate (DEM), 590 g of DMF and 743 g (7.5 mol) of DCE is heated to 115° C. and 1620 g (5.0 mol) of a 21 percent by weight solution of sodium ethylate in ethanol are metered in over 7 hours, with stirring. An azeotrope containing about 37 percent by weight of ethanol and about 63 percent by weight of DCE is removed by distillation under normal pressure at about 75° C. The azeotrope is condensed and passed through an aqueous ethanol solution in the top receiver to extract the ethanol. The lower phase, consisting predominantly of DCE, is recycled to the top of the column. Part of the aqueous phase is continuously drawn off and replaced with fresh water. The ethanol is removed by distillation from the aqueous phase, rendered anhydrous and used for the reaction.

The reaction mixture is allowed to react for a further 30 minutes at 115° C. and then allowed to cool to room temperature. The salt which has precipitated out is filtered, washed with DMF and DCE and dried to give 230 g (97.9% of theory) of sodium chloride, which is suitable for chloro alkali electrolysis.

DCE is removed first by distillation from the filtrate and wash liquors under normal pressure. DMF and unreacted DEM then distill over under vacuum as the intermediate fraction. 318 g of the target product, ECD, distill over last at 96° C./16 mbar. The purity is 99.4% according to GC analysis and the yield corresponds to 68.1% of theory. Taking into account the DEM contained in the intermediate fraction, the yield is 85.8% of theory.

EXAMPLE 5

Preparation of Dimethyl 2-methylcyclopropane-1,1-dicarboxylate (MMCD)

The reaction is carried out in the apparatus described in Example 1. A mixture of 264.2 g (2.0 mol) of DMM, 590 g of DMF and 677.4 g (6.0 mol) of 1,2-dichloropropane is heated to 114° C. and 720 g (4.0 mol) of a 30 percent by weight solution of sodium methylate in methanol are metered in over 6 hours, with stirring. The azeotrope of methanol and 1,2-dichloropropane distill at 55.5° C. To extract the methanol, water is introduced continuously into the top receiver acting as a phase separation vessel, and a corresponding amount of aqueous-alcoholic phase is drawn off.

The product is worked up in the manner described and the salt which has precipitated is washed with DMF and dried to give 230 g of sodium chloride, corresponding to 98.4% of theory. The filtrate and wash liquor are distilled via a column under a water-jet vacuum to give 106 g of MMCD as the main fraction at 88° C./14 mbar. The purity is 98.4% according to GC analysis and the yield is 30.4% of theory, based on the DMM used. Taking into account 46 g of DMM recovered as the intermediate fraction, the yield is 36.8% of theory.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for the preparation of a cyclopropane-1,1-dicarboxylic acid derivative, comprising:

reacting a malonic acid derivative and a 1,2-dichloro compound of formula III

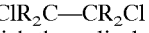

$ClR_2C—CR_2Cl$ in which the radicals R can be identical or different and are in each case hydrogen or an organic radical with an alcoholate as a condensation agent which is gradually added to a mixture of said malonic acid derivative and said 1,2-dichloro compound as a solution or suspension in an alcohol.

2. The process of claim 1, wherein the reaction is conducted in an inert solvent.

3. The process as claimed in claim 1, wherein the malonic acid compound, the 1,2-dichloro compound and the alcoholate are present in molar ratios of 1:(2.0–6.0):(1.6–2.0).

4. The process as claimed in claim 1, wherein the alcoholate is an alkali metal alcoholate in the form of a 20 to 40 percent by weight solution or suspension in the alcohol from which the alkali metal alcoholate is derived.

5. The process as claimed in claim 1, wherein the reaction temperature is 80° to 140° C.

6. The process as claimed in claim 5, wherein the temperature is 95° to 120° C.

7. The process as claimed in claim 1, wherein said 1,2-dichloro compound and alcohol are removed by distillation from the reaction mixture during the reaction.

8. The process as claimed in claim 7, wherein the alcohol is extracted with water from the mixture of 1,2-dichloro compound and alcohol, the 1,2-dichloro compound is transferred to the top of the distillation column and the alcohol is obtained in a re-usable form from the aqueous alcohol solution by distillation if the two substances form an azeotrope.

9. The process as claimed in claim 7, wherein both 1,2-dichloro compound and alcohol are obtained in a re-usable form from the mixture of 1,2-dichloro compound and alcohol by fractional distillation if the two substances do not form an azeotrope.

10. The process as claimed in claim 1, wherein the malonic acid compound has the formula:

in which X and Y, which can be the same or different, are selected from the group consisting of carboxylic acid ester, nitrile and an optionally N-substituted carboxamide group.

11. The process as claimed in claim 1, wherein the 1,2-dichloro compound has the formula:

$$\begin{array}{c} CR_2Cl \\ | \\ CR_2Cl \end{array} \qquad \text{III}$$

wherein the R groups are the same or different and are selected from the group consisting of hydrogen and an organic radical.

12. The process as claimed in claim 11, wherein the organic radical is an alkyl of 1 to 8 carbon atoms, or the R groups together form an alkylene radical of 5 to 12 carbon atoms.

13. The process as claimed in claim 11, wherein said 1,2-dichloro compound is 1,2-dichloroethane, 1,2-dichloropropane, 1,2-dichlorobutane, 2,3-dichlorobutane, 2,3-dichloropentane, 2-methyl-1,2-dichlorobutane, 1,2-dichlorooctane, 1,2-dichlorocyclopentane, 1,2-dichlorocyclohexane, 1,2-dichlorocyclododecane, 1,2-dichloroethylbenzene or 1,2-dichloroisopropylbenzene.

14. The process as claimed in claim 1, wherein said alcoholate is an alkali metal alcoholate of 1 to 4 carbon atoms.

* * * * *